US005732703A

United States Patent [19]

Kalfas et al.

[11] Patent Number: 5,732,703
[45] Date of Patent: *Mar. 31, 1998

[54] STEREOTAXY WAND AND TOOL GUIDE

[75] Inventors: Iain H. Kalfas, Beachwood; Donald W. Kormos, Parma; David W. Piraino, Shaker Heights; Gene H. Barnett, Gates Mills; Charles P. Steiner, Pepper Pike, all of Ohio

[73] Assignee: The Cleveland Clinic Foundation, Cleveland, Ohio

[*] Notice: The term of this patent shall not extend beyond the expiration date of Pat. No. 5,517,990.

[21] Appl. No.: 650,455

[22] Filed: May 20, 1996

Related U.S. Application Data

[63] Continuation-in-part of Ser. No. 224,955, Apr. 8, 1994, Pat. No. 5,517,990, which is a continuation-in-part of Ser. No. 983,390, Nov. 30, 1992, Pat. No. 5,309,913.

[51] Int. Cl.$^6$ .................................................. A61B 6/00
[52] U.S. Cl. ................................... 128/653.1; 606/130
[58] Field of Search ........................ 128/653.1, 653.2, 128/653.4, 653.5, 654; 606/130; 364/413.13, 413.22

[56] References Cited

U.S. PATENT DOCUMENTS

| 4,722,056 | 1/1988 | Roberts et al. | 364/413 |
|---|---|---|---|
| 4,793,355 | 12/1988 | Crum et al. | 128/653 |
| 4,896,673 | 1/1990 | Rose et al. | 128/660.03 |
| 5,099,846 | 3/1992 | Hardy | 128/653.1 |
| 5,143,076 | 9/1992 | Hardy et al. | 128/664 |
| 5,230,338 | 7/1993 | Allen et al. | 128/653 |
| 5,257,998 | 11/1993 | Ota et al. | 606/130 |
| 5,383,454 | 1/1995 | Bucholz | 128/653.1 |
| 5,517,990 | 5/1996 | Kalkas et al. | 128/653.1 |
| 5,622,170 | 4/1997 | Schulz . | |

FOREIGN PATENT DOCUMENTS

| WO 90/05494 | 5/1990 | WIPO . |
|---|---|---|
| WO 91/04711 | 4/1991 | WIPO . |

OTHER PUBLICATIONS

"A Computer–Assisted System for 3–D Frameless Localization in Stereotaxic MRI" Clarysse, et al. IEEE Transactions on Medical Imaging, vol. 10, No. 4, Dec. 1991.

"A Frameless, Armless Navigational System for Computer–Assisted Neurosurgery", Kato, et al. J. Neurosurg 74:845–849, May, 1991.

Cass Computer Assisted Stereotactic Surgery, MIDCO Medical Instrumentation and Diagnostics Corporation, advertising brochure, 1992.

"A Frameless Stereotaxic Operating Microscope for Neurosurgery", Friets, et al., IEEE Transactions on BioMedical Engineering, vol. 36, No. 6, Jun. 1989, pp. 608–617.

"Reference–Display System for the Integration of CT Scanning and the Operating Microscope", Masters Thesis of John Hatch, Dartmouth College, Oct. 1984.

*Primary Examiner*—Ruth S. Smith
*Attorney, Agent, or Firm*—Fay, Sharpe, Beall, Fagan, Minnich & McKee

[57] ABSTRACT

A patient is secured to a subject support (10). A stereotaxic wand (40) is inserted into a tool guide (60). The wand has a tip portion (44), a portion extending along a pointing axis (46) of the wand, an offset portion (42) which is offset from the pointing axis of the wand, and at least three wand emitters (48, 50, 52), mounted in alignment with the pointing axis of the wand. The three emitters selectively emit infrared light which is received by two CCD cameras (14) mounted to a frame assembly (12). The tool guide includes a bore (76) extending along a guide axis. The bore is configured for selectively receiving a tool and the tip portion of the wand. An entry point and a trajectory are identified by the surgeon with the wand in the guide. More specifically, a trajectory and location of the wand are superimposed on a diagnostic image on a monitor (30). If the surgeon is satisfied with the entry point and trajectory shown on the monitor, a surgical tool is inserted into the bore while the tool guide is held along the designated trajectory and at the designated entry point.

21 Claims, 7 Drawing Sheets

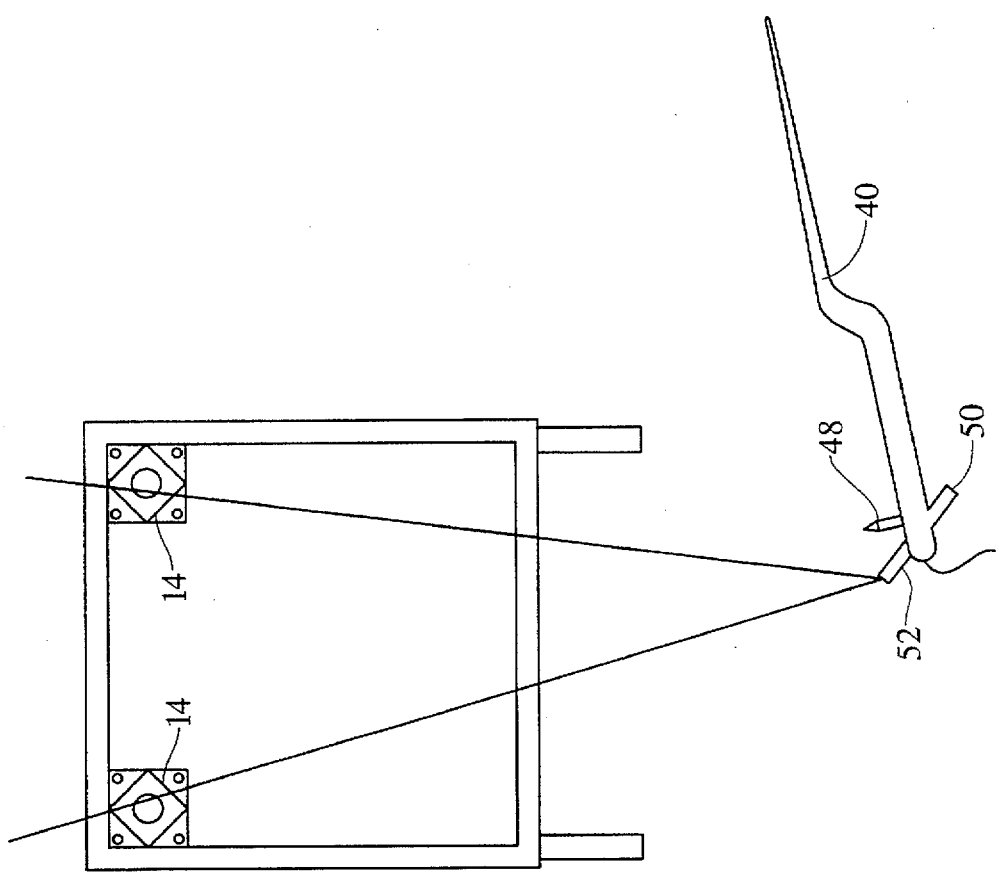
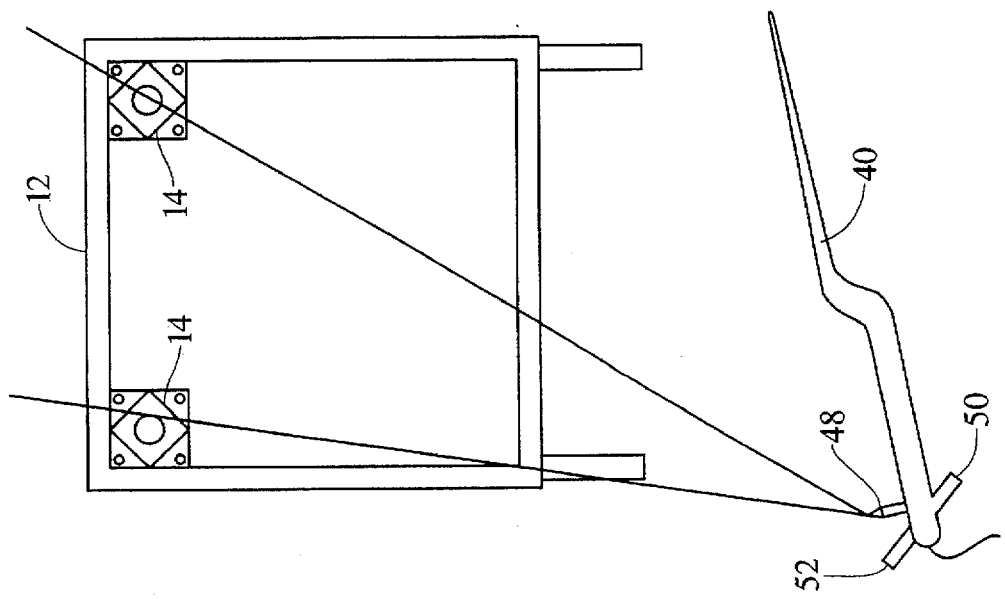

STEREOTAXY WAND AND TOOL GUIDE

This application, a continuation-in-part of U.S. application Ser. No. 08/224,955, filed Apr. 8, 1994, now U.S. Pat. No. 5,517,990 which, in turn, is a continuation-in-part of U.S. Application Ser. No. 07/983,390, filed Nov. 30, 1992, now U.S. Pat. No. 5,309,913.

BACKGROUND OF THE INVENTION

The present invention relates to the medical diagnostic and surgical arts. It finds particular application in conjunction with neurosurgery and will be described with particular reference thereto. However, it is to be appreciated, that the invention will also find application in conjunction with neurobiopsy, CT-table needle body biopsy, breast biopsy, endoscopic procedures, orthopedic surgery, other invasive medical procedures, industrial quality control procedures, and the like.

Three-dimensional diagnostic image data of the brain, spinal cord, and other body portions is produced by CT scanners, magnetic resonance imagers, and other medical diagnostic equipment. These imaging modalities typically provide structural detail with a resolution of a millimeter or better.

Various frameless stereotactic procedures have been developed which take advantage of the three-dimensional image data of the patient. These procedures include guided-needle biopsies, shunt placements, craniotomies for lesion or tumor resection, and the like. Another area of frameless stereotaxy procedure which requires extreme accuracy is spinal surgery, including screw fixation, fracture decompression, and spinal tumor removal.

In spinal screw fixation procedures, for example, surgeons or other medical personnel drill and tap a hole in spinal vertebra into which the screw is to be placed. The surgeon relies heavily on his own skill in placing and orienting the bit of the surgical drill prior to forming the hole in the vertebra. Success depends largely upon the surgeon's estimation of anatomical location and orientation in the operative field. This approach has led to suboptimal placement of screws that may injure nerves, blood vessels, or the spinal cord.

The present invention provides a new and improved technique which overcomes the above-referenced problems and others.

SUMMARY OF THE INVENTION

According to one aspect of the present application, a stereotaxic wand is provided. The wand has a tip portion, a portion extending along a pointing axis of the wand, an offset portion which is offset from the pointing axis of the wand, and at least three wand emitters. The three wand emitters selectively emit wand signals which are received by at least two receivers positioned on a frame assembly. The frame assembly mounts the receivers in a fixed relationship to a subject support closely adjacent a means for securing a portion of the patient to the subject support. A wand position determining means determines a position of the wand tip portion from the intersection of the emitter signals between the wand emitters and the two receivers mounted on the frame. A tool guide defines a bore extending longitudinally therethrough along a guide axis. The bore is configured for selectively receiving either a tool or the tip portion of the wand.

According to another aspect of the present application, the tool guide includes teeth on one end to inhibit the guide from slipping on bone.

One advantage of the present application is that it facilitates more accurate surgical procedures.

Another advantage of the present invention is that it promotes patient safety.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIGS. 3A and 3B are diagrammatic illustrations of the wand and locator relationship;

DETAILED DESCRIPTION OF THE PREFERRED EMBODIMENTS

Figure 1A:
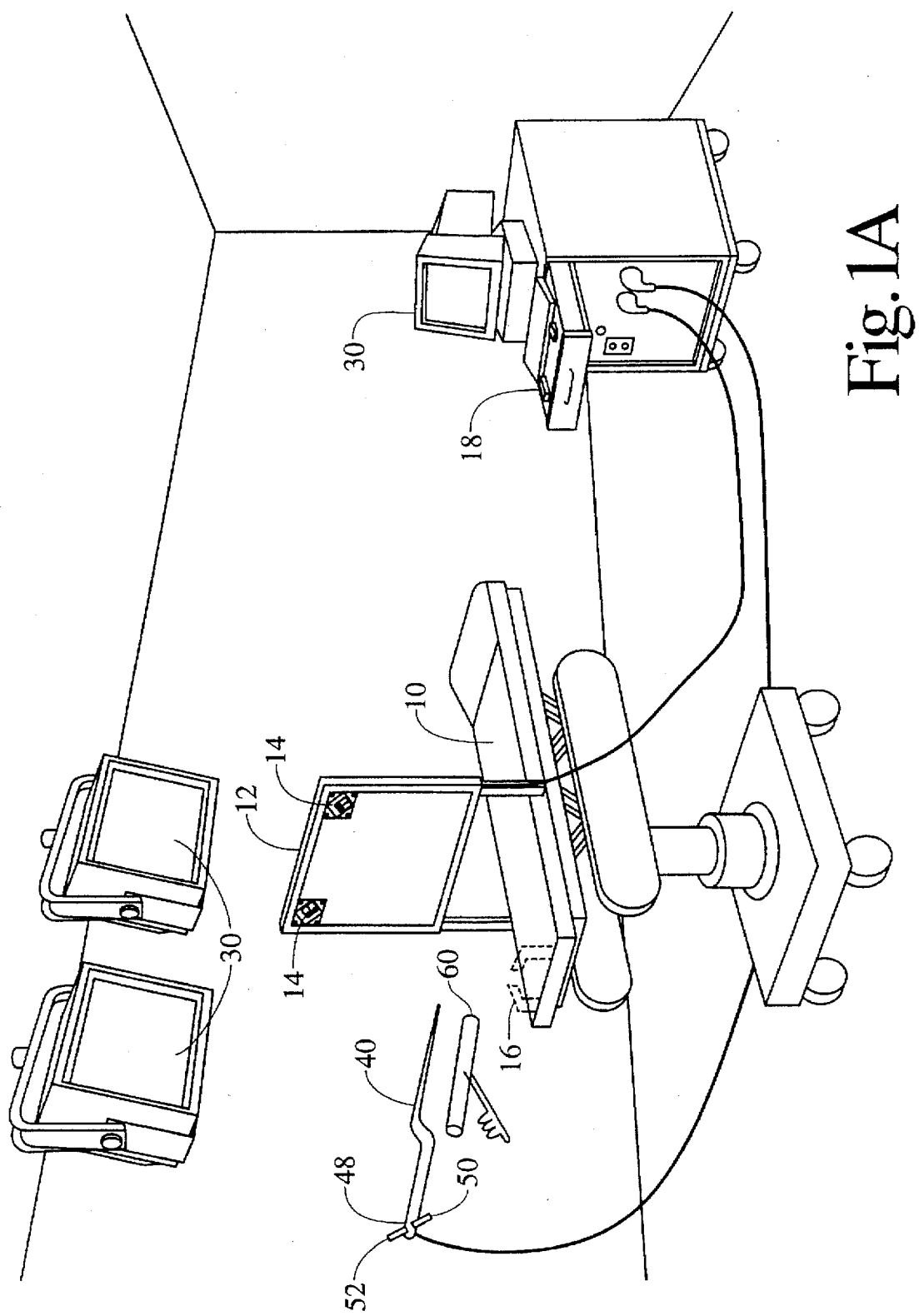
FIG. 1A is a perspective view of an operating room in which the present invention is deployed.

With reference to FIG. 1A, a subject, such as a human patient, is received on an operating table or other subject support 10 and appropriately positioned within the operating room. A frame 12 is mounted in a fixed relationship to the patient such that it is precisely positioned within the subject or subject support coordinate system. In the illustrated embodiment, the frame 12 is mounted to the patient support 10. Mounting the frame 12 to the patient support permits the patient support to be turned, raised, lowered, wheeled to another location, or the like, without altering the patient coordinate system. Alternately, the support may be mounted to a pole or other stationary support, the ceiling of the room, or the like. The frame 12 supports a plurality of receivers 14 such as charge-coupled device (CCD) arrays, infra-red cameras, light sensitive diodes, other light sensitive receivers, and the like mounted at fixed, known locations thereon. Alternately, the receivers can receive other types of radiant energy such as ultrasound, X-rays, radiation, radio, magnetics, or the like. A securing means such as a head clamp 16, securely positions a portion of the subject under consideration. The frame is mounted at a fixed or selectable angle from vertical such that the frame is positionable more toward the patient, yet still focusing on the region of interest of the patient.

Figure 1B:
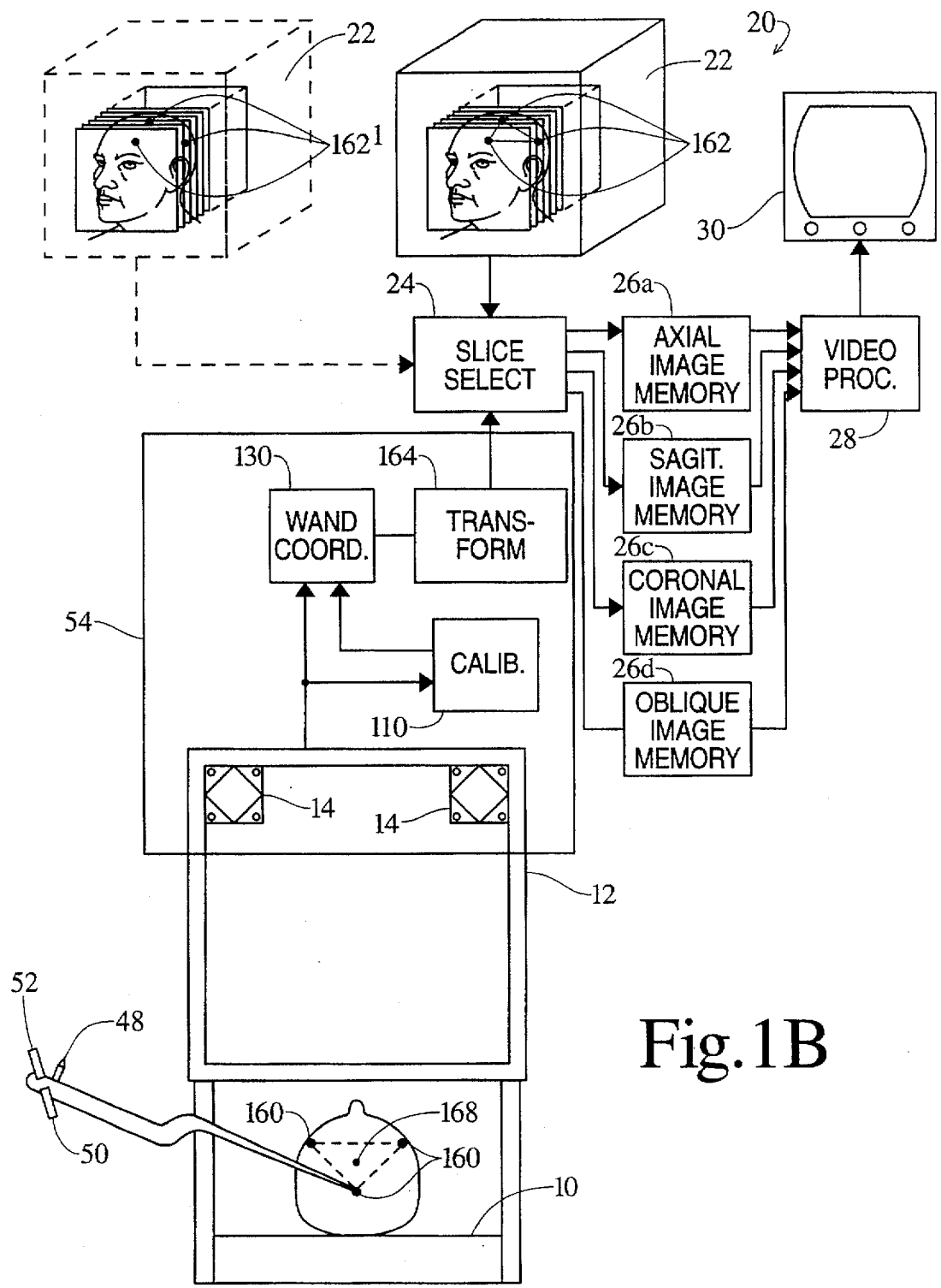
FIG. 1B is a block diagram of the image data manipulation of the system of FIG. 1A.

With continuing reference to FIG. 1A and further reference to FIG. 1B, an operator console 18 houses a computer system 20. Alternately, the computer system can be remotely located and connected with the control console 18 by cabling. The computer system includes a three-dimensional data memory 22. The stored three-dimensional image data preferably contains a video pixel value for each pixel or point in a three-dimensional rectangular grid of points, preferably a 256×256×256 grid. When each image value represents one millimeter cube, the image data represents about a 25.6 centimeter cube through the patient with one millimeter resolution. Because the data is in a three-dimensional rectangular grid, selectable orthogonal and other oblique planes of the data can readily be withdrawn from the three-dimensional memory using conventional technology. A plane or slice selector 24 selects various two-dimensional planes of pixel values from the three-dimensional memory for display.

The plane or slice selector preferably selects at least: axial, sagittal, coronal, and oblique planes through a selectable point of the patient. The pixel values which lie on the selected axial, sagittal, coronal, and oblique planes are copied into corresponding image memories 26a, 26b, 26c, and 26d. A video processor 28 converts the two-dimensional digital image representations from one or more of image memories 26 into appropriate signals for display on video monitors 30 or other appropriate image displays.

Figure 2A:
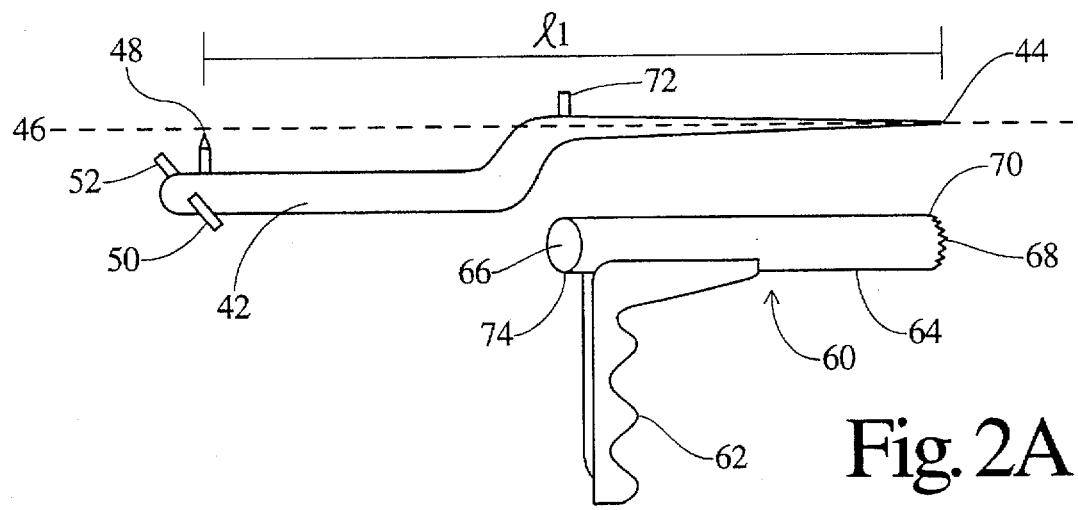
FIGS. 2A, 2B, 2C, 2D, 2E, and 2F illustrate alternate embodiments of the wand and guide.

With continuing reference to FIG. 1A and further reference to FIG. 2A, a wand 40, formed of suitable resilient material such as metal, has an offset handle portion 42 and a tip portion or proximal end 44. The offset handle 42 is connected to a portion extending along a pointing axis 46 of the wand. In this preferred embodiment, a first emitter 4e is mounted on the pointing axis 46 while two other emitters 50 and 52 are mounted off the axis. Each emitter selectively emits an infra-red signal that is received by the receivers 14. The first emitter 48 is located at $x_1, Y_1, z_1$ along the axis 46 a fixed known distance $l_1$ from the tip 44. The second emitter 50 may then be calculated to be at $x_1+\Delta x_2, y_1+\Delta y_2, Z_1+\Delta Z_2$ (where $\Delta+x_2, \Delta Y_2$ and $\Delta z_2$ represent constant values based on the geometry of the second emitter relative to the tip). The third emitter 52 is at $x_1+\Delta x_{33}, y_{1i}+\Delta y_3, z_1+\Delta z_3$ (where $\Delta x_3, \Delta Y_3$ and $\Delta z_3$ represent constant values based on the geometry of the third emitter relative to the tip).

Emitters 48, 50, and 52 emit infra-red positioning signals used by a locator system 54 to locate a coordinate and trajectory of the wand. Infra-red signals are received from each of the emitters at the two receivers. The three infra-red signals received by each receiver are used to calculate the axis 46 and the location of the tip. The plane or slice selector 24 (FIG. 1B) selects patient image planes based on the coordinate and trajectory located. It is to be appreciated that more than three emitters may be mounted on the wand to provide additional positioning signals to be used by a locator system to locate the coordinate and trajectory of the wand.

The wand 40 is readily sterilized by conventional techniques. It is used in conjunction with a guide 60 to designate a coordinate and trajectory at which a surgical tool will be applied to the patient. The guide can be any guide or appliance which positions the wand 40 to establish a surgical trajectory. In the preferred embodiment, the guide 60 is a portable tool which has a hand-shaped handle 62 which extends from the drill guide, a tube member 64 which defines an internal bore 66 to receive and accurately position the wand, and teeth 68 at the distal end 70 of the bore to reduce the possibility of the guide slipping on bone. The bore 66 of the tool guide has a diameter which allows for the non-simultaneous insertion of either the wand 40 or a surgical tool such as a drill, biopsy needle, and the like. Rather than being hand-held, the guide 60 can be mounted to other structures in the operating room, e.g. framed stereotaxic equipment or a mechanical brace. In intraoperative use, the wand 40 is inserted in the tool guide bore until the tip 44 aligns with the tool guide distal end 70. A wand stop 72 is positioned on the wand and abuts a proximal end surface 74 of the tool guide when the wand tip aligns with the distal end 70.

With the wand tip aligned with the tool guide end, the surgeon commences probing the patient to seek an optimal coordinate and trajectory in which to insert the appropriate surgical tool. To this end, the surgeon maneuvers the wand and tool guide in combination to a proposed trajectory and actuates the emitters. Signals from the emitters are used to calculate the trajectory 46 and the end point 44 of the wand. The trajectory and end point are displayed on the monitor 30 superimposed on the three-dimensional image or selected image plane(s).

By viewing the display 30, the surgeon identifies the location of the wand tip with respect to anatomic structure, and the trajectory of the bore. If the trajectory is unsatisfactory, the wand is repositioned and its new trajectory determined and evaluated. This approach improves surgical planning when compared with prior approaches in which surgeons relied solely on their own estimation of the patient's anatomy. Following the identification of a satisfactory trajectory and coordinate, the wand 40 is removed from the bore 66 of the guide 60 while the guide is held in position. Holding the guide 60 steady preserves the appropriate trajectory and position coordinates in the axial and sagittal planes determined by the wand. Thereafter, the appropriate surgical tool or appliance is inserted within the guide 60. With this approach, the surgical tool is properly positioned in the appropriate trajectory for performing the surgical procedure.

The wand and tool guide are particularly useful in accurately identifying the optimal entry point, trajectory, the depth of insertion of screws to be placed into the patient's spinal column, the depth of insertion of a biopsy needle, and the like.

Figure 2B:
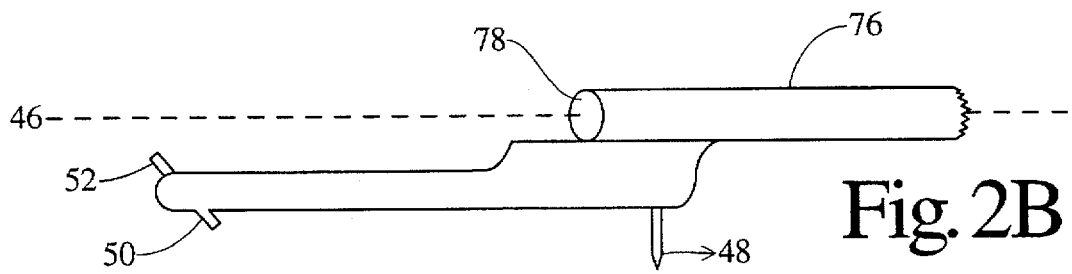
Figure 2C:
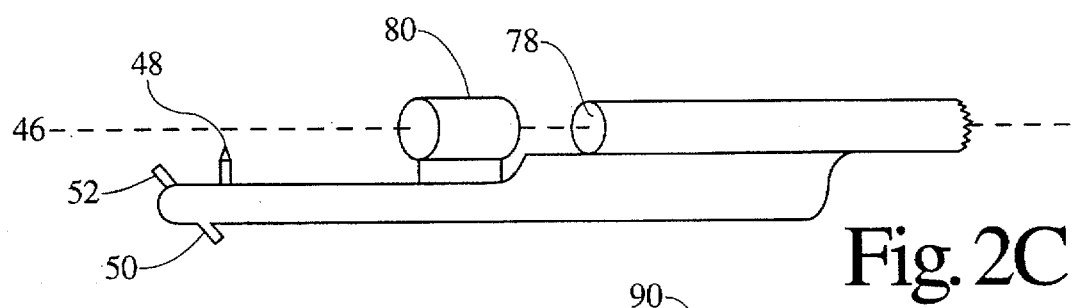
Figure 2D:
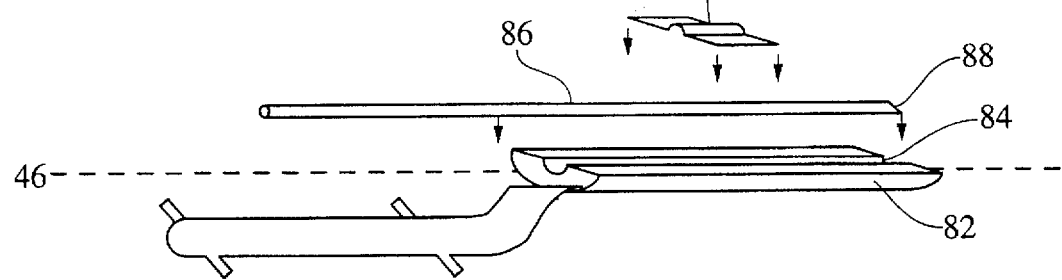

With reference to FIGS. 2B, 2C, and 2D alternative embodiments of the present invention are shown in which the guide is integrated into the wand. In general, each of the alternative embodiments contain a wand offset portion on which are mounted at least three emitters for emitting positioning signals. In the illustrated embodiments, the central axis or pointing direction 46 aligns with a longitudinal axis of the guide means formed integrally with the wand for simplicity of use.

With reference to FIG. 2B, a tubular portion 76 is integrated with the wand. The tubular portion defines a bore 78 extending along its longitudinal axis. In intraoperative use, the surgeon probes the patient with the distal end seeking to locate the proper coordinate and trajectory for the surgical tool. Once the coordinate and trajectory are located, the surgeon holds the offset portion while the surgical tool is inserted within the tube. Thereafter, the surgical tool is operated to perform the surgical procedure.

With reference to FIG. 2C, a second alterative embodiment is shown similar to the previously described alternative embodiment. However, in addition to the structure previously described, a laser 80 is mounted to the offset portion. Light emitting from the laser travels along the longitudinal pointing axis 46 of the bore 78 of the tubular member to provide a visual indication of trajectory in the patient coordinate system. In intraoperative use, the surgeon maneuvers the integrated wand and laser while viewing images displayed on the monitor 30. The images selected for display are based upon the coordinate and trajectory of the bore center point at the proximal end of the integrated wand.

With reference to FIG. 2D, another embodiment is shown in which a grooved guide member position 82 is incorporated into the wand. The grooved member is connected to the offset portion. The grooved member contains a groove 84 having a longitudinal axis which is in line with pointing axis 46 of the wand. This alternative embodiment finds particular usefulness in conjunction with needle biopsies. In intraoperative use, a biopsy needle 86 is positioned within the groove so that a tip 88 of the biopsy needle 86 aligns with the groove center point at the proximal end of the integrated wand. The biopsy needle is held in place by a restraining means such as Velcro®straps 90 attached to the sides of the grooved member.

Figure 2E:
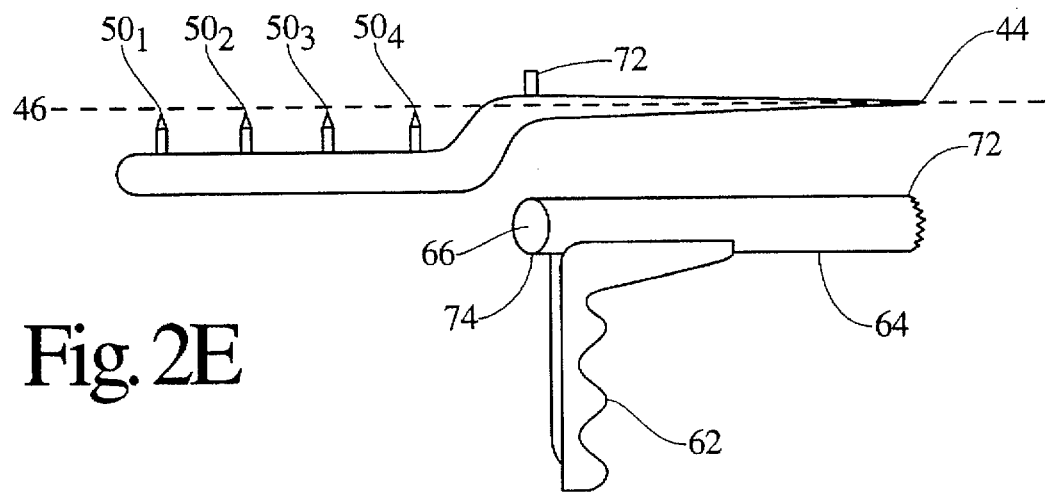
Figure 2F:
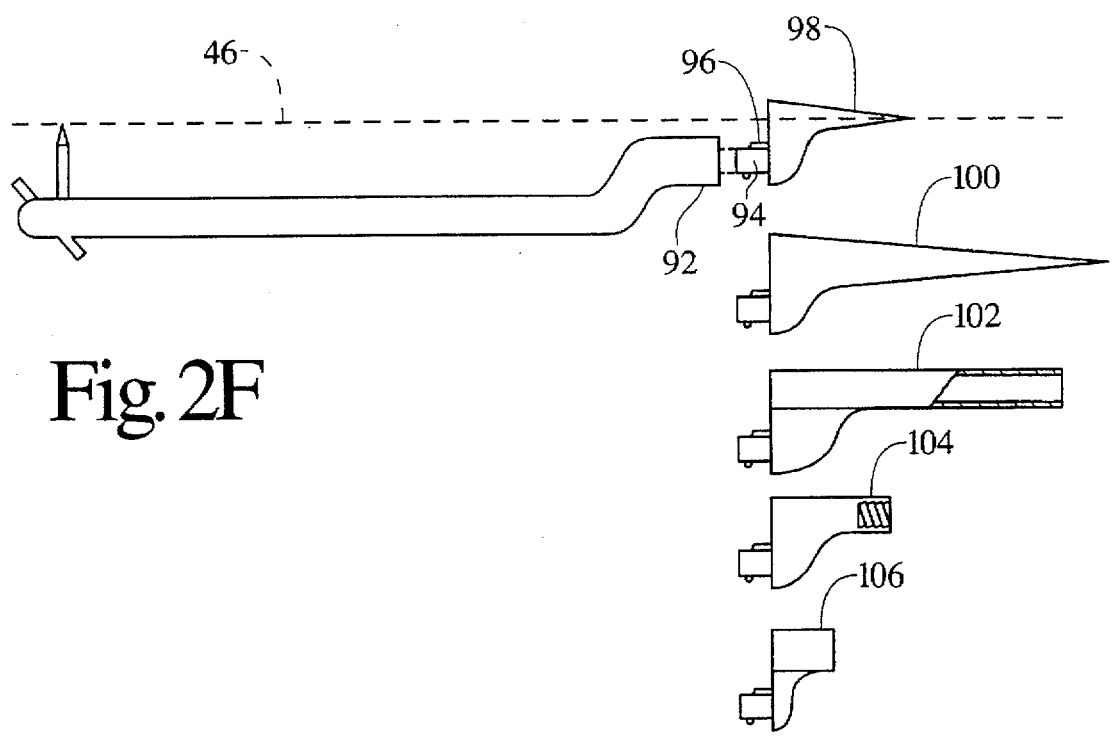

In the embodiment of FIG. 2E, the wand has emitters $50_1$, $50_2$, $50_3$, $50_4$, mounted along the axis 46. Although any two emitters would determine the axis 46, greater accuracy is obtained by redundantly determining the axis 46 and averaging the results. Preferably, a least squares fit is used to compensate for any deviation in the axis 46 determined by the various emitter pairs. In the embodiment of FIG. 2F, the wand has interchangeable tips. The wand includes a first connector portion 92 which selectively connects with a second connector portion 94 of the tips. Various connector systems are contemplated such as a threaded bore and threaded shaft, a snap lock connector means, bayonet connector, spring lock, or other connector systems. A key and keyway system 96 or other means for fixing the alignment of the tips and the wand is particularly advantageous when the connector is off the axis 46.

Various tips are contemplated. A short tip 98 is provided for accurate registration. A longer tip 100 facilitates reaching deeper into interior regions of the subject. Tubular drill guides 102 can be provided in various diameters to accommodate different size drills. An adapter 104 enables endoscopes and other tools to be attached to the wand. Tools and equipment, such as an array of ultrasonic transducers 106, can be connected to the adaptor 104 or configured for direct connection to the wand. A wide variety of other tips for various applications are also contemplated.

The preferred embodiment uses the stereotaxic wand 40 to align the coordinate system of the operating room including the patient, the tool guide, and wand with the coordinate system of a previously prepared three-dimensional image stored in memory. Prior to identifying the proper coordinate and trajectory of the tool guide, the patient space is aligned with or referenced to the stored three-dimensional image data preferably using the following technique.

FIG. 3A illustrates infra-red CCD array cameras as receivers 14 which are mounted on the frame 12. The location of the wand emitters in the coordinate system of the frame and patient, hence the position of the wand axes and tip relative to the patient, is determined by the intersection of the light rays traveling between the emitter 48, 50 and 52 and the two infra-red CCD array camera receivers 14. For example, emitter 48 emits an infra-red signal which is received by both infra-red CCD array cameras 14. From the cameras' perspective, the two infra-red signals intersect at a single point. Preferably, a least squares fit is used to determine the point of intersection. This point of intersection is the location of the emitter 48.

Figure 3C:
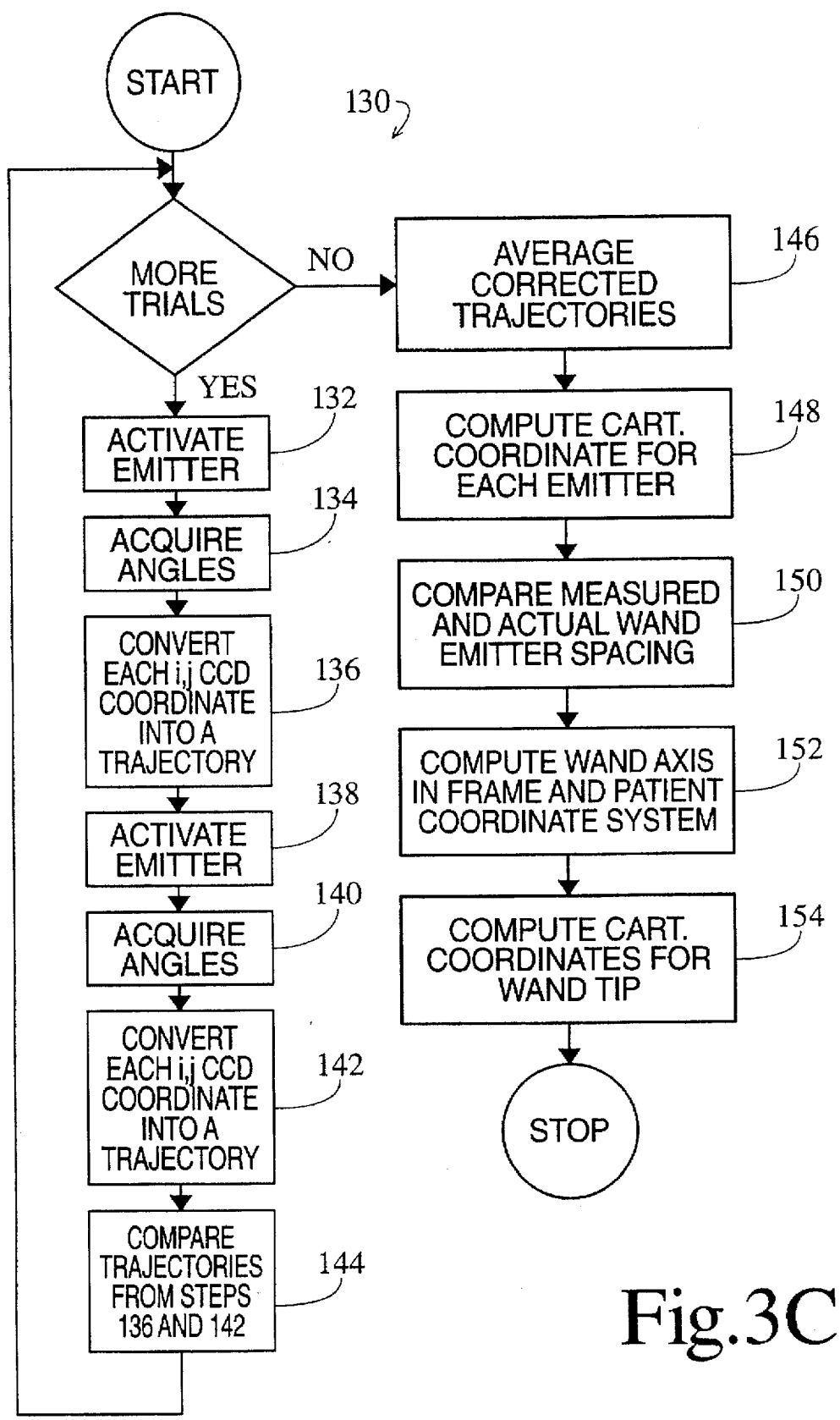
FIGS. 3C is a flow diagram of the wand location procedure.

With reference to FIGS. 3A, 3B, and 3C, a wand coordinate and trajectory determining procedure 130 determines the coordinate positions of the three emitters 48, 50 and 52, the central axis and the wand tip. More specifically, a step 13 causes the emitters to emit an infra-red signal. The CCD array receivers 14 on the frame 12 receive the infra-red signals. A step 134 acquires the (i, j,) coordinate locations on the CCD array at which each ray is received. From prior calibration, a step 136 converts each (i,j) CCD coordinate into a trajectory. A step 138 causes the emitters to emit an infra-red signal again. A step 140 acquires another set of CCD coordinates and a step 142 determines another pair of trajectories. A step 144 compares the trajectories from steps 136 and 144. If the trajectories fail to match within a preselected tolerance, steps 132-144 are repeated.

If the trajectories are within the preselected tolerance of being the same in the two acquisitions, an averaging step 146 averages the trajectories between each of the wand emitters 48, 50 and 52 and each of the CCD array receivers 14. From these trajectories, a step 148 calculates the Cartesian coordinates $(x_1,y_1,z_1)$ in the frame or patient coordinate system for the three emitters 48, 50 and 52.

A step 150 checks the validity of the measurement. More specifically, the known separation between the wand emitters is compared with the separation between the measured coordinates $x_1,y_1,z_1$, $x_2,y_2,z_2$ and $X_3,y_3,Z_3$ of the wand emitters. If the difference between measured and known separation of any two emitters is greater than the acceptable error, e.g. 0.75 mm when measuring with a resolution of 1 mm, an erroneous measurement signal is given. The measurement is discarded and the surgeon or other user is flagged to perform the measurement process 130 again. From the coordinates of the three emitters 48, 50 and 52, and from the geometry of the wand discussed in conjunction with FIG. 2, a step 152 calculates the wand axis in the frame and patient coordinate system. A step 154 calculates the Cartesian coordinates $(x_0,y_0,z_0)$ for the wand tip 44.

Figure 4A:
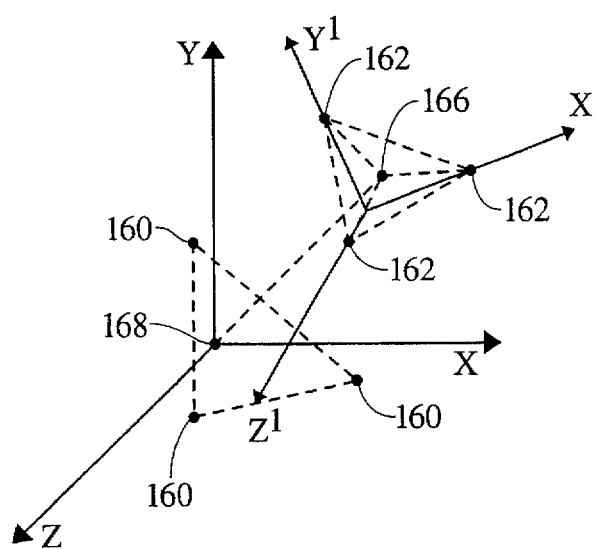
FIGS. 4A, 4B, 4C, and 4D are illustrative of a preferred coordinate transform between the coordinate system of the data and the patient.

With reference to FIG. 4A, before the wand and tool guide can be used to locate a proper coordinate and trajectory for a surgical tool such as a drill, the patient space or coordinate system (x,y,z) is aligned with the image space or coordinate system (x', y', z') stored in memory. Aligning the spaces begins with referencing known positions or points 160 in the patient space with the wand tip. For example, the tip 44 of the wand may be referenced to three independent positions of the vertebra, i.e. the tips of the spinous and traverse processes. These positions 160 on the vertebra are compared with the corresponding position of pixels 162 in the image space. Fiducials can also be used to make the corresponding coordinates in patient space and image space. To this end, three or more fiducials or markers are affixed at three or more spaced points on the patient's body. The fiducials are visible in the imaging medium selected such that they show up as readily identifiable dots 162 in the resultant image data. The fiducials are markers or small beads that are injected with radiation opaque and magnetic resonance excitable materials. A small dot or tattoo is made on the patient's skin and a fiducial is glued to each dot. This enables the position 160 of the fiducials to be denoted even if the fiducials are removed in the interval between the collection of the image data and the surgical procedure. Thereafter, a transform 164, as shown in FIG. 1B, transforms the coordinates of the patient space into the coordinate system of the image space. To align the patient and image spaces, the tip of the wand is placed on each fiducial, tattooed marker point, or characteristic vertebra point 160.

With reference to FIGS. 4A-4D, the position of the three fiducials or process tips 160 are compared with the relative position of the pixels 162 in the image space. Actuating the emitters while the tip of the wand is touching each of its characteristic patient space points x, y, z defines these points electronically. Like coordinates x',y',z' of the pixels 162 are defined electronically from the electronic image and compared to the patient space coordinates x,y,z. The translation and rotational relationship between image space and patient space coordinate systems is determined. With reference to FIG. 4A, the position of the patient in operating room space (x,y,z) and the relative position in image space (x',y',z') are determined. That is, the transform between the two coordinate systems are defined. The translation means first determines the offsets $X_{offset}$, $Y_{offset}$, $Z_{offset}$ between the barycenters 166, 168 of the triangles defined by the coordinates of three fiducials or process tips in data and patient space, respectively. This provides a translation or an offset in the x, y, and z-directions between the two coordinate systems. The values of $X_{offset}$, $Y_{offset}$, and $Z_{offset}$ are added or subtracted to the coordinates of the patient space and the coordinates of image space, respectively, to translate between the two.

Figure 4B:
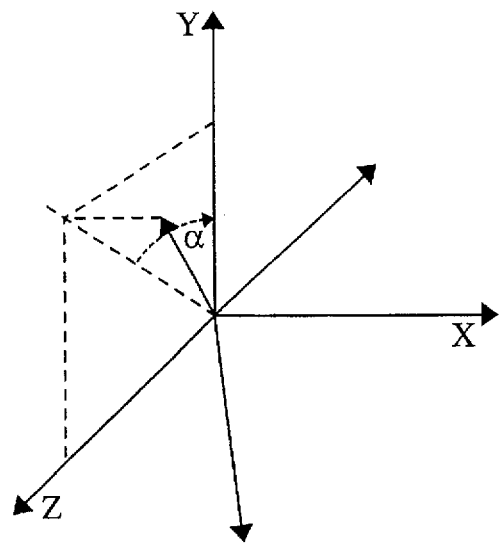
Figure 4C:
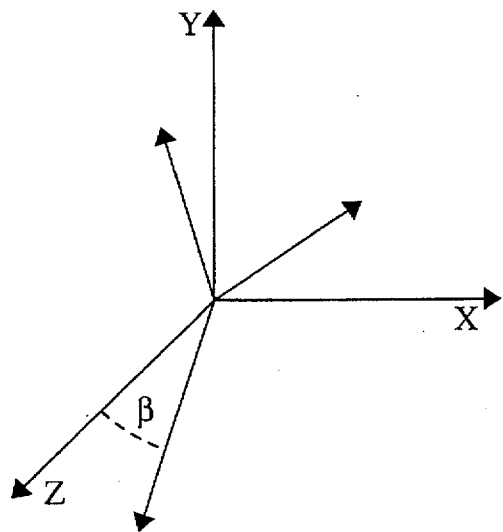
Figure 4D:
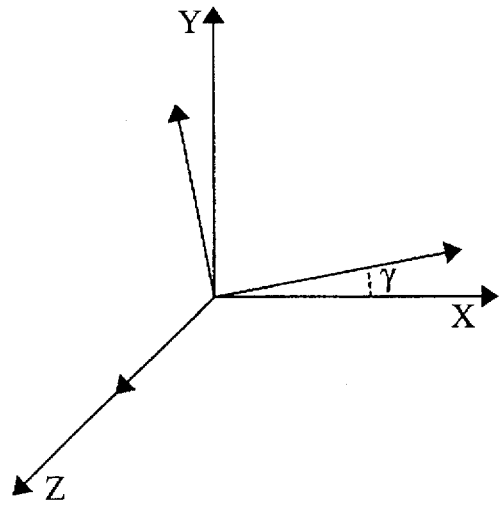

With reference to FIG. 4B, translating the origins of the two coordinate systems into alignment, however, is not the complete correction. Rather, the coordinate systems are normally also rotated relative to each other about all three axes whose origin is at the barycenter. As illustrated in FIGS. 4B, 4C, and 4D, the angle of rotation in the (y,z), (x,z), and (x,y) planes are determined. Having made these determinations, it is a simple matter to transform the patient support space coordinates into the image space coordinates and, conversely, to rotate the image space coordinates into patient space coordinates. The wand coordinate means 130 is connected through the transform 164 with one of the plane selecting means 24 and the video processor 28 to cause a marker, e.g. cross hairs, to be displayed on the monitors 30 at the coordinates of the wand tip. This enables the surgeon to coordinate specific points on the patient or in the incision with the images.

Having aligned the image and patient spaces, the wand and tool guide can be used to identify the entry coordinate and trajectory at which the surgical tool will be applied to the patient. For example, the surgeon may use the wand and tool guide in combination to identify the trajectory and coordinate on the spinal column at which the surgeon will utilize a surgical drill in order to drill a hole for the placement of a spinal screw. Holding the wand and drill guide in one hand, the surgeon moves the combination around the exposed vertebra while viewing images displayed on a monitor selected in accordance with the wand tip. The images provide a cross-sectional view of the vertebra and allow the surgeon to plan with greater accuracy the angle and depth at which the drill will be operated. Once the coordinate and trajectory of the drill application is identified, the surgeon may remove the wand while holding the tool guide in place. Since the tool guide comes with a handle, the surgeon can hold the tool guide in place even when the spinal column moves in response to patient breathing. In other words, the surgeon can easily hold the bore of the tool guide at the trajectory identified even while the spinal column experiences movement. With the guide properly oriented, the surgeon inserts into the bore the surgical tool and tip needed for the spinal screw fixation. This technique is superior over prior methods in which surgeons relied solely on their own skill and knowledge of the patient's unique anatomy and will result in far fewer sub-optimal results.

The present invention is also useful in preplanning a surgical operation. For example, surgeons may use images of the body portion at which the surgical tool will be inserted in order to determine prior to the operation, the best trajectory and coordinate at which the tool should be applied. Once the proper trajection and coordinate are identified, the computer system can store these images in memory to be later used as a reference target to be compared with images produced in connection with the wand and drill guide. In particular, the images produced in accordance with the wand and drill guide could be compared with the stored images until the computer identifies an image match. Once the computer identifies a match, the computer can output a signal to alert the surgeon that the tool guide has been properly oriented.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for designating a coordinate and trajectory on a subject and for guiding a tool at the coordinate and along the trajectory as the tool is applied to the subject, the system comprising:
   a subject support;
   a means for securing a preselected portion of the subject to the subject support;
   a frame assembly which mounts at least two receivers in a fixed relationship to the subject;
   a wand defining a tip portion and a pointing axis of the wand, and having at least three wand emitters mounted in a spaced relationship in a fixed relationship to the pointing axis and the tip, the emitters selectively emitting wand signals which are received by the at least two receivers;
   a guide defining a path extending longitudinally along a guide axis, the path being configured for selectively receiving a tool and the tip portion;
   a wand position determining means for determining a position of the wand tip portion from the wand signals from the wand emitters which are received by the at least two receivers.

2. The system as set forth in claim 1 further including teeth on one end of the guide for engaging the subject to inhibit the guide from slipping.

3. The system as set forth in claim 1 wherein the emitters emit light.

4. The system as set forth in claim 3 wherein the receivers include CCD arrays.

5. The system as set forth in claim 4 further including a circuit connected with the receiver for determining trajectories between the emitters and the receivers.

6. The system as set forth in claim 1 further including:
   a three-dimensional image memory means for storing image data indicative of a three-dimensional region of the portion of the subject which is secured to the subject support means;
   a plane selecting means for selecting planar slices of data from the three-dimensional, image memory means;
   a display means for converting the selected slices of data from the plane selecting means into human-readable displays; and
   a transform means for transforming a position of the wand pointer into a coordinate system of the image data stored in the three-dimensional image memory means, the transform means being operatively connected with the plane selecting means such that the displayed images have a preselected relationship to a position of the wand.

7. The system as set forth in claim 6 further including:
   at least three markers disposed at selected subject portions when the three-dimensional image data was acquired such that locations of the three markers are identifiable in the three-dimensional image data; and a transform calculating means for calculating a transform between positions of the markers on the subject denoted by selectively placing the wand tips on each of the markers with the marker locations in the three-dimensional image data, whereby translational and rotational relationships between a subject space coordinate system and a three-dimensional image data space coordinate system.

8. In a system including a pointer which defines a pointing axis and having a plurality of signal emitters connected therewith, a plurality of receivers for receiving signals emitted by the emitters, and a position determining means for determining an orientation of the pointing axis, an apparatus for orienting a tool and guiding an application of the tool to a subject, the apparatus comprising:

a guide for guiding a tool along a guide axis, said guide having a means for selectively receiving and constraining the pointer with the pointer axis aligned with the guide axis.

9. The system as set forth in claim 8 wherein the guide and the pointer are integrally connected.

10. The system as set forth in claim 8 wherein the receivers include video cameras.

11. An apparatus for guiding an application of a tool to a subject from an entry point along a trajectory, the apparatus comprising:

a guide member defining a guide axis and having a distal end positionable on a selected subject entry point, said guide member being configured to support a tool along the guide axis;

a means for holding, the distal end of the guide member at the selected entry point and for holding the guide axis steady;

a signaling means for sending light signals indicative of the guide axis;

a means for receiving the light signals and determining an orientation of the guide axis;

a means for storing a diagnostic image of the subject;

a correlating means for correlating the determined orientation of the guide axis with a coordinate system of the diagnostic data; and a display means for displaying a selected portion of the diagnostic data with the guide axis superimposed thereon.

12. An apparatus for guiding an application of a tool to a subject from an entry point along a trajectory, the apparatus comprising:

a guide member defining a guide axis and having a distal end positionable on a selected subject entry point, said guide member being configured to support a tool along the guide axis;

a means for holding the distal end at the selected entry point and for holding the guide axis steady;

a signaling means for indicating a location of the guide member, the signaling means including:
  a wand which is configured for receipt in the guide member;
  at least three emitters affixed to the wand, in a preselected relationship to the guide axis;
  at least two receivers for receiving signals emitted by the emitters; and
  a means for determining the guide axis from the received signals;

a means for storing a diagnostic image of the subject;

a correlating means for correlating the guide axis with a coordinate system of the diagnostic data; and a display means for displaying a selected portion of the diagnostic data with the guide axis superimposed thereon.

13. The apparatus as set forth in claim 12 wherein the guide member includes teeth at the distal end of the guide member.

14. An apparatus for guiding an application of a tool to a subject from an entry point along a trajectory the apparatus comprising:

a guide member defining a guide axis and having a distal end, said guide member being configured to support a tool along the guide axis;

a means for fixedly holding the distal end of the guide member at a selected location and orientation relative selected entry point into the subject; and a correlating means for correlating the guide axis with a coordinate system of the diagnostic data, the correlating means including:
  at least a pair of light sources mounted in a fixed relationship to each other and to the guide member;
  at least a pair of light receiving means for receiving the light from the light sources;
  a circuit for determining trajectories along which light travels between each light source and each light receiving means; and
  a means for determining locations of the light sources from intersections of the trajectories and for determining at least an orientation of the guide axis from the determined light source locations.

15. A method of orienting a tool and guiding an application of the tool to a subject, the method comprising:

a) maneuvering a guide to a proposed entry point and a proposed trajectory for application of the tool;

b) sending signals which are indicative of the proposed trajectory and the proposed entry point;

c) receiving the signals and deriving a signaled entry point and a signaled trajectory therefrom;

d) correlating the signaled entry point and the signaled trajectory with electronic diagnostic image data of the subject stored in computer memory;

e) generating a human-readable display of at least a portion of the image data with the trajectory and entry point superimposed thereon;

f) inserting the tool into the guide while maintaining the guide steady at the proposed entry point and trajectory; and g) applying the tool to the subject through the guide along the proposed trajectory to the proposed entry point.

16. A method of orienting a tool and guiding an application of the tool to a subject, the method comprising:

a) inserting a pointing portion of a wand into guide, the wand carrying a plurality of radiant energy emitters;

b) maneuvering the guide and wand such that the pointing portion indicates a proposed entry point and trajectory for application of a tool;

c) signaling the trajectory and entry point, the signaling step including:
  c1) actuating the emitters to emit radiant energy signals;
  c2) receiving the radiant energy signals at least at two fixed locations relative to the subject;
  c3) calculating locations of the emitters from the received radiant energy signals; and
  c4) calculating the proposed trajectory and the proposed entry point from the locations of the emitters;

d) correlating the signaled entry point and trajectory with electronic diagnostic image data of the subject stored in computer memory;

e) generating a human-readable display of at least a portion of the image data with the trajectory and entry point superimposed thereon;

f) inserting the tool into the guide while maintaining the guide steady at the proposed entry point and trajectory; and g) applying the tool to the subject through the guide along the proposed trajectory to the proposed entry point.

17. The method as set forth in claim 16 wherein the radiant energy signal is infrared light.

18. The method as set forth in claim 16 wherein the step c3) of calculating the emitter locations includes:

calculating trajectories between the two fixed locations at which radiant energy signals are received and the emitters; and determining intersections of the trajectories.

19. A tool guide for orienting a tool and guiding the tool along a selected trajectory to a subject, the tool guide comprising:

a guide member which receives and constrains a tool to a fixed orientation relative to an axis defined on the guide member; and a plurality of light sources mounted to the guide member in a fixed relationship to each other, the light sources emitting light of a distinguishable characteristic.

20. The tool guide as set forth in claim 19 wherein the light sources are LED's and the emitted light has the distinguishable characteristic of being infrared light.

21. In combination a tool guide for constraining a tool to a fixed orientation relative thereto, a means for holding the tool guide and tool in a fixed relationship relative to a subject, the tool guide having a plurality of light sources in a fixed relationship mounted thereto, and a system for generating a human readable display of diagnostic images of the subject with at least a trajectory of the tool superimposed thereon, the system including:

diagnostic image data representative of the diagnostic images of the subject;

a memory for storing the diagnostic image data;

a plurality of light receivers which receive light from the light sources, the receivers being mounted in a fixed relationship to the subject;

a circuit connected to the light receives for determining a location of the light sources relative to the light receivers and at least a trajectory of the tool relative to the subject;

a circuit for superimposing an indication of at least the trajectory of the tool and the diagnostic image data; and a monitor for converting the superimposed trajectory indication and diagnostic image data into a human readable display.

* * * * *